(12) United States Patent
Iwagaki et al.

(10) Patent No.: US 9,061,165 B2
(45) Date of Patent: Jun. 23, 2015

(54) SOLUTION FOR FORMING DOUBLE EYELID AND METHOD FOR FORMING DOUBLE EYELID USING SAME

(76) Inventors: Naoko Iwagaki, Tokyo (JP); Masayuki Kamagata, Tokyo (JP); Jirou Taniyama, Kanagawa (JP)

(*) Notice: Subject to any disclaimer, the term of this patent is extended or adjusted under 35 U.S.C. 154(b) by 0 days.

(21) Appl. No.: 13/124,611

(22) PCT Filed: Jan. 27, 2010

(86) PCT No.: PCT/JP2010/051033
§ 371 (c)(1),
(2), (4) Date: Apr. 15, 2011

(87) PCT Pub. No.: WO2010/087365
PCT Pub. Date: Aug. 5, 2010

(65) Prior Publication Data
US 2011/0271973 A1 Nov. 10, 2011

(30) Foreign Application Priority Data
Jan. 28, 2009 (JP) .................................. 2009-017327

(51) Int. Cl.
A61K 8/73 (2006.01)
A61K 8/37 (2006.01)
(Continued)

(52) U.S. Cl.
CPC . *A61Q 1/10* (2013.01); *A61K 8/027* (2013.01); *A61K 8/34* (2013.01); *A61K 8/731* (2013.01)
USPC ........... 514/788; 514/471; 514/772; 514/781; 514/785; 132/320

(58) Field of Classification Search
None
See application file for complete search history.

(56) References Cited

U.S. PATENT DOCUMENTS 3,736,946 A * 6/1973 Yando et al. .................... 132/73
3,846,404 A 11/1974 Nichols
(Continued)

FOREIGN PATENT DOCUMENTS

JP 47-046911 11/1972
JP 47-46911 * 11/1972
(Continued)

OTHER PUBLICATIONS

Ono et al., Translation of JP 47-046911, issued Nov. 27, 1972 Ono.*
(Continued)

*Primary Examiner* — Rachael E Bredefeld
*Assistant Examiner* — Dominic Lazaro
(74) *Attorney, Agent, or Firm* — Fitch, Even, Tabin & Flannery, LLP

(57) ABSTRACT

To provide a solution for forming a double eyelid which enables extremely easy formation of a natural and ideal double eyelid without giving a displeased feeling or an uncomfortable feeling to a user, and a method for forming a double eyelid using the solution for forming a double eyelid. A solution for forming a double eyelid 1 according to the present invention is formed by dissolving, into a solvent having volatility, a fibrous material which forms a film 1a onto a skin 5a of an eyelid 5 and shrinks with vaporization of the solvent. By applying the solution 1, in a successive-curve form, over an imaginary line I forming a fold 5d of a double eyelid in the eyelid 5 onto which a user want to make a fold and vaporizing the solvent so as to shrink the film 1a, successive concaved groove-like constricted part 5c is formed on the imaginary line I and the fold 5d of a double eyelid along the constricted part 5c is formed.

11 Claims, 2 Drawing Sheets

(51) Int. Cl.
*A61Q 90/00* (2009.01)
*A61K 8/34* (2006.01)
*A61Q 1/10* (2006.01)
*A61K 8/02* (2006.01)

(56) References Cited

U.S. PATENT DOCUMENTS

2006/0165626 A1* 7/2006 Ricard et al. ............... 424/70.11
2007/0148120 A1* 6/2007 Omura et al. .............. 424/70.16

FOREIGN PATENT DOCUMENTS

| JP | 47-046911 | B | | 11/1972 |
|----|-----------|---|---|---------|
| JP | 59-502092 | A | | 12/1984 |
| JP | 62-136545 | A | | 8/1987 |
| JP | 02-188512 | A | | 7/1990 |
| JP | 02-240011 | A | | 9/1990 |
| JP | 10-304935 | A | | 11/1998 |
| JP | 11-171728 | A | | 6/1999 |
| JP | 11171728 | A | * | 6/1999 |
| JP | 3277180 | A | | 2/2002 |
| JP | 3111511 | U | | 7/2005 |
| JP | 2006188512 | A | | 7/2006 |
| JP | 2007-106711 | A | | 4/2007 |
| JP | 2008-208076 | A | | 9/2008 |
| JP | 2009022592 | | | 2/2009 |
| WO | 84/01891 | A | | 5/1984 |
| WO | WO 92 03509 | | * | 5/1992 |

OTHER PUBLICATIONS

English Language Translation of JP 11-171728 A.*
Office Action for Japanese Application No. 2010-548530 issued on Jul. 17, 2012.
Office Action for Japanese Application No. 201080002887.8 issued on Apr. 1, 2012.
Office Action for Korean Application No. 2011-7010460 issued on Jan. 22, 2013.
Chinese Office Action for Application No. 201080002887.8 issued Apr. 1, 2012.
Chinese Office Action for Application No. 201080002887.8 issued Nov. 16, 2012.
Japanese Office Action for Application No. 2010-548530 issued Nov. 5, 2012.
International Search Report dated Apr. 13, 2010 for PCT/JP2010/051033.
Russian Office Action for Application No. 2011135846 (4 pages).
Allen MJ et al., Cholelitholysis using methyl tertiary butyl ether. Gastroenterology., 1986, 88 (1 Pt 1), p. 122-5, abstract, found in PubMed-D3.

* cited by examiner

SOLUTION FOR FORMING DOUBLE EYELID AND METHOD FOR FORMING DOUBLE EYELID USING SAME

CROSS REFERENCE TO RELATED APPLICATIONS

This application is a national phase application of International Application No. PCT/JP2010/051033, filed Jan. 27, 2010, claiming priority to Japanese Application No. 2009-017327, filed Jan. 28, 2009, both of which are incorporated by reference herein in their entirety.

TECHNICAL FIELD

The present invention relates to liquid cosmetics for forming a double eyelid used for forming a double eyelid, and to a method for forming a double eyelid using the same. More specifically, the present invention relates to a solution for forming a double eyelid, the solution enabling extremely easy formation of a natural and ideal double eyelid by being applied onto a skin of an eyelid onto which a user want to make a fold, and relates to a method for forming a double eyelid using the solution for forming a double eyelid.

BACKGROUND ART

Cosmetics for making a single eyelid double can be classified mainly into a type of applying a solution onto a skin of an eyelid and a type of sticking a tape-like article on the skin of the eyelid. The former solution type has already been known as solutions described in Japanese Patent Application Laid-open No. 2007-106711, Japanese Patent Application Laid-open No. Hei 11-171728, and Japanese Patent Application Publication No. Hei 06-062384. The latter tape type has already been known as tapes described in Japanese Patent Application Laid-open No. Sho 59-502092, Japanese Patent Application Laid-open No. Hei 10-304935, and a microfilm of Japanese Utility Model Application No. Sho 61-024573 (Japanese Utility Model Application Laid-open No. Sho 62-136545).

Further, the above-mentioned solution type can be classified mainly into a type of forming a fold of a double eyelid by being applied onto the skin of the eyelid to thereby adhere skins together, and a type of forming a fold of the double eyelid by being applied onto the skin of the eyelid to thereby form a coating harder than the skin of the eyelid so as to form a crease of the skin along the upper edge of the coating when the eyelid is opened.

In addition, the above-mentioned tape-type can also be classified mainly into a type of forming a fold of a double eyelid by adhering skins of the eyelid together with a double-sided adhesive tape, and a type of forming a fold of a double eyelid by sticking onto the skin of the eyelid a tape harder than the skin of the eyelid to thereby form a crease of the skin along the upper edge of the tape when the eyelid is opened.

However, these conventional solution-type and tape-type cosmetics for forming a double eyelid forcibly formed a fold of a double eyelid mainly by utilizing the coating or adhesiveness and hardness of the tape. Therefore, there have been problems that an unnatural double eyelid is liable to be formed and a displeased feeling and an uncomfortable feeling are given to a user.

In order to solve the above-mentioned problems, the Applicant proposed a double-eyelid forming article in Japanese Patent No. 3277180, which was completely different type from the conventional types. The double-eyelid forming article utilizes a resilient shrinkability of a resin tape or a string to shrink and deform a skin of an eyelid together with tissue directly under the skin. Then, the tape or the string is made to bite into the skin of the eyelid so as to form a constricted part along the tape or the string. As a result, when the eyelid is opened, the skin of the eyelid is naturally folded back at the constricted part to thereby form a fold of a double eyelid. As a result, compared with the conventional types, the double-eyelid forming article enabled formation of the more natural double eyelid without giving a displeased feeling or an uncomfortable feeling to the user.

However, use of the double-eyelid forming article requires a series of manipulation's including pinching both ends of the double-eyelid forming article with fingertips of both hands, sticking the double-eyelid forming article onto the skin of the eyelid while stretching the double-eyelid forming article, and thereafter cutting surplus parts at the both ends. Therefore, unaccustomed users sometimes have a little difficulty in handling the article, so the double-eyelid forming article leaves much room for further improvements.

SUMMARY OF THE INVENTION

Problem to be Solved by the Invention

A technical object of the present invention is to provide a solution for forming a double eyelid which enables extremely easy formation of a natural and ideal double eyelid without giving a displeased feeling or an uncomfortable feeling to a user, and a method for forming a double eyelid using the solution for forming a double eyelid.

Means for Solving the Problem

In order to obtain the above-mentioned object, a solution for forming a double eyelid according to the present invention provides a solution for forming a double eyelid for forming a double eyelid by being applied to a skin of an eyelid, the solution according to the present invention includes: a solvent having volatility; and a base material which is dissolved in the solvent and forms a film closely adhered onto the skin of the eyelid with vaporization of the solvent, in which the base material having solubility contains a fibrous material which shrinks with vaporization of the solvent, and the film shrinks by shrinkage of the fibrous material with the film being closely adhered onto the skin of the eyelid.

In this case, in the solution for forming a double eyelid, it is desirable that a shrinking ratio of the film on the skin of the eyelid range from 10% or more to 15% or less, and the film after shrinkage have resilient shrinkability and nonsticky.

Further, it is desirable that the base material be constituted only by the fibrous material, and content of the fibrous material occupied in the whole solution for forming a double eyelid preferably range from 5 weight % or more to 25 weight % or less.

Further, the fibrous material preferably be cellulose or a derivative thereof, more preferably be cellulose ester, and particularly preferably be nitrocellulose.

It is desirable that the solvent vaporizes by a body temperature.

Specifically, the solvent desirably be one kind selected from ethanol and ethyl acetate, or a mixture of ethanol and ethyl acetate.

Further, in order to achieve the above-mentioned object, a method for forming a double eyelid using the solution for forming a double eyelid according to the present invention includes: applying a solution for forming a double eyelid to a skin of an eyelid onto which a user want to make a fold, the solution for forming a double eyelid being formed by dissolving, into a solvent having volatility, a base material shrinking with vaporization of the solvent; vaporizing the solvent to thereby shrink a film made of the base material with the film being closely adhered onto the skin of the eyelid; forming, by shrinkage of the film, a concaved constricted part on the skin of the eyelid; and folding back the skin of the eyelid at the constricted part to thereby form a fold of the double eyelid.

Effects of the Invention

According to the present invention, by merely applying a solution for forming a double eyelid to a skin onto which a user want to make a fold and vaporizing the solvent, a film of a base material adhered onto the skin of the eyelid shrinks to thereby form a concaved constricted part at the part on the skin onto which the film is adhered.
As a result, when the eyelid is opened, the skin of the eyelid is folded back at the constricted part, and hence a fold of a double eyelid can be formed.

As described above, the constricted part is formed at the part onto which the film is adhered with the effect of shrinkage of the film of the base material. Therefore, substantially entire of the film after shrinkage is disposed inside the constricted part and the usage state is hard to be noticed on appearance. In addition, when the eyelid is opened, the skin of the eyelid is naturally folded back at the constricted part to thereby form the fold of the double eyelid, and therefore a displeased feeling and an uncomfortable feeling are not given to the user.

Consequently, the present invention enables extremely easy formation of a natural and ideal double eyelid without giving a displeased feeling and an uncomfortable feeling to the user.

Further, the fibrous material is also superior in affinity for other cosmetics, and hence makeup holds well also on the part onto which the film 1a is adhered.

MODES FOR CARRYING OUT THE INVENTION

Figure 1:
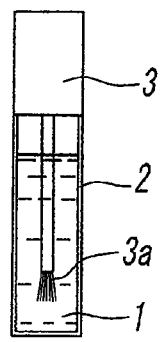
FIG. 1 is a sectional view showing a container containing a solution for forming a double eyelid according to the present invention.

Hereinafter, an embodiment of a solution for forming a double eyelid according to the present invention is described in detail.

The solution for forming the double eyelid according to the present invention is provided for forming a fold of a double eyelid by being applied, onto the skin of an upper eyelid onto which a user want to make a fold, along the edge of the eyelid. The solution for forming the double eyelid according to the present invention mainly includes a solvent having volatility and a base material which is dissolved in the solvent and forms a film closely adhered onto the skin of the eyelid with vaporization of the solvent, the base material thereby contributing to formation of the fold of the double eyelid. Further, the base material mainly includes a fibrous material exhibiting shrinkability with vaporization of the solvent.

Therefore, shrinkage of the fibrous material with vaporization of the solvent causes the entire film made of the base material to shrink while closely adhering onto the skin of the eyelid. With the effect of the shrinkage, a concaved constricted part is formed on the skin of the eyelid onto which the film is adhered. As a result, when a user opens the eyelid, the skin of the eyelid is naturally folded back at the constricted part so that a fold of a double eyelid is formed. In this case, the film after shrinkage is mainly formed of the fibrous material in a shrunk state. Therefore, the film has resilient shrinkability and flexibility, and hence, it also has excellent adaptability to movement and expansion and contraction of the skin of the eyelid.

In this case, it is necessary that the film of the base material shrink while entirely being adhered closely onto the skin of the eyelid and the closely-adhered state to the skin be kept even if the eyelid is opened and closed after shrinkage. Accordingly, the film has close-adhesiveness to the skin, which prevents the film from exfoliating from the skin of the eyelid during shrinkage thereof or when the eyelid is opened and closed in an average user. At the same time, the film has a shrinking force which is larger than a tension (resilient force) on a surface of the skin of the eyelid and smaller than a shrinking force which forms wrinkles with shrinkage of the film in the direction of intersecting with the constricted part, the wrinkles being unnecessary for forming the fold of the double eyelid. More specifically, it is preferable that shrinking ratio of the film on the skin with vaporization of the solvent range from 10% or more to 15% or less. When the shrinking ratio is smaller than 10%, the shrinking force is excessively small, which causes a fear that a constricted part having a sufficient depth for forming the fold of the double eyelid is not formed. On the other hand, when the shrinking ratio is larger than 15%, the shrinking force is excessively large, which causes a fear that the constricted part becomes too deep and makes the appearance unnatural and gives the user a displeased feeling or an uncomfortable feeling. Further, it also causes the above-described fear that the wrinkles unnecessary for forming the fold of the eyelid are formed in the direction of intersecting with the constricted part.

In addition, in order to efficiently utilize effective properties of the fibrous material such as shrinkability so as to form a film which is ideal for forming a natural double eyelid on the skin of the eyelid, it is desirable that the solution for forming a double eyelid contain as little as possible, except for the case there is a necessity, film-forming ingredients having solubility to the solvent and acting in a direction of obstructing the effective properties of the fibrous material. Therefore, it is ideal that the base material having solubility to the solvent be composed only of the fibrous material. However, this does not hinder addition of soluble additives such as a moisturizing agent, antiseptic, perfume, pigments, and the like to the solution for forming a double eyelid within a range of substantially not obstructing effective properties of the fibrous material, the soluble additives being capable of forming a part of the film by remaining on the skin together with the fibrous material after vaporization of the solvent.

Further, similarly, it is also possible to add matters such as lamé which do not have solubility to the solvent and remain on the skin together with the base material such as fibrous material after vaporization of the solvent to the solution for forming a double eyelid within the range of substantially not obstructing the effective properties of the fibrous material.

Further, in order to form a natural and ideal double eyelid without giving a displeased felling like a sticky feeling, it is preferable that the film after shrinkage be nonsticking and nonadhesive as a rule. Therefore, it is preferable that the above-mentioned solution for forming a double eyelid do not contain sticking ingredients and adhesive ingredients as a rule.

It should be noted that, when the base material is composed only of the fibrous material, the content of the fibrous material occupied in the entire solution for forming a double eyelid preferably range from 5 weight % or more to 25 weight % or less, and more preferably range from 15 weight % or more to 25 weight % or less. When the content of the fibrous material is smaller than 5%, ratio of shrinkage with vaporization of the solvent becomes too small to form a fold of a double eyelid. On the other hand, when the content of the fibrous material is larger than 5%, the stickiness of the solution becomes so large that the solution lacks practicability.

As the above-mentioned fibrous material, cellulose or derivative thereof is suitably used. More preferably, cellulose ester such as nitrocellulose, cellulose acetate (acetyl cellulose), cellulose acetate butyrate (CAB), and cellulose acetate propionate (CAP) are used. Of these, the nitrocellulose is particularly preferably used.

However, the fibrous material is not particularly limited to the cellulose. Materials which can be directly applied to the skin, have solubility to the solvent, and exhibit shrinkability with vaporization of the solvent may be used. Further, combination of a plurality of kinds of fibrous materials filling the above conditions may also be used.

On the other hand, specific examples of the above-mentioned solvent can include one kind or a mixture of two kinds or more selected from oxyacid esters such as alpha-hydroxyisobutyric acid butyl, alpha-hydroxyisobutyric acid ethyl, alpha-hydroxyisobutyric acid isopropyl, methyl lactate, ethyl lactate, isopropyl lactate, butyl lactate, glycolic acid methyl, glycolic acid ethyl, glycolic acid isopropyl, and glycolic acid buthyl; ketones such as camphor, acetone, methyl ethyl ketone (MEK), methyl-n-propyl ketone, methyl isobutyl ketone (MIBK), methyl isoamyl ketone, cyclohexanone, diisobutyl ketone, and C-11 Ketone; esters such as ethyl acetate, isopropyl acetate, n-propyl acetate, n-butyl acetate, isobutyl isobutyrate, hexyl acetate, ethylethoxypropionate, 2-ethylhexyl acetate, dibasic acid ester, and texanol ester alcohol; glycol ethers such as propylene glycol monomethyl ether, ethylene glycol monomethyl ether, propylene glycol mono t-butyl ether, ethylene glycol monopropyl ether, propylene glycol monopropyl ether, propylene glycol monobutyl ether diethylene glycol monomethyl ether, dipropylene glycol monometyl ether, and diethylene glycol monobutyl ether; glycol ether esters such as propylen glycol monomethyl ether acetate, ethylen glycol monoethyl ether acetate, ethylen glycol monobutyl ether acetate, ethylene glycol diacetate, diethylene glycol monoethyl ether acetate, and diethylene glycol monobuthyl ether acetate; alcohols such as methanol, ethanol, isopropanol, n-butanol, and isobutanol; and water.

Further, of these specific examples, one kind or a mixture of two kinds or more selected from ethanol, methanol, ethyl acetate, camphor, ether, and acetone are preferably used, and one kind or mixtures selected from ethanol and ethyl acetate are more preferably used.

However, the above-mentioned solvent is not limited to the specific examples mentioned above, and materials having volatility, being directly applicable to the skin, and capable of dissolving the fibrous material may be used. However, it is desirable that the material have volatility at room temperature or body temperature so that vaporization is further promoted when the solution is applied to the skin of the eyelid.

Hereinafter, with reference to FIGS. 1 to 7, one example of methods of forming a double eyelid by the solution for forming a double eyelid is described in detail including the principle thereof.

It should be noted that, in this example, there is used a solution for forming a double eyelid 1 constituted by dissolving, as a soluble base material, 15 weight % of nitrocellulose which is a fibrous material with respect to 85 weight % of ethanol which is a solvent.

In the above-mentioned solution for forming a double eyelid 1, the solvent has volatility at room temperature. Therefore, as illustrated in FIG. 1, at the time of nonuse the solution 1 is accommodated in a container 2 having tolerance to liquid medicines, and an opening (not shown) thereof is closed by a cap 3 in the airtight state. Further, a brush as an application means 3a for the solution 1 is fixed to the cap 3, and the application means 3a is provided in the container 2 and is immersed in the solution 1 in the container 2 when the cap is closed.

However, forms of the container 2 for accommodating the solution 1 and the application means 3a for applying the solution 1 are not limited to the above. For example, the entire container 2 may be a pen type or the like, and the application means 3a may be a spatula type, a sponge type, or the like.

Figure 2:
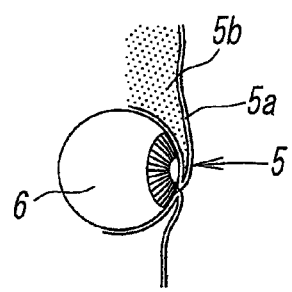
FIG. 2 is a sectional view showing an eyelid before applying thereon the solution for forming a double eyelid according to the present invention.

Incidentally, as illustrated in FIG. 2, an eyelid 5 (which means an upper eyelid in this case) of human roughly has a skin 5a and tissue 5b such as a layer of fat provided inside thereof, and the skin 5a is formed into a curved surface along the surface of an eyeball 6. The eyelid can be opened and closed by expanding and contracting muscles (not shown).

In forming a double eyelid by applying the solution 1 to the eyelid 5, firstly, grease, dirt, makeup and the like stuck on the surface of the skin 5a of the eyelids to which a user want to make a fold are eliminated by face-washing or the like. Then, an imaginary line I extending from the adjacency of the inner corner of the eye to the adjacency of the outer corner of the eye is determined at the position along the edge of the eyelid at which a fold 5d of the double eyelid is to be formed. In this case, use of a thin pole-like stick (not shown) when required makes the determination of the imaginary line I easier.

Figure 3:
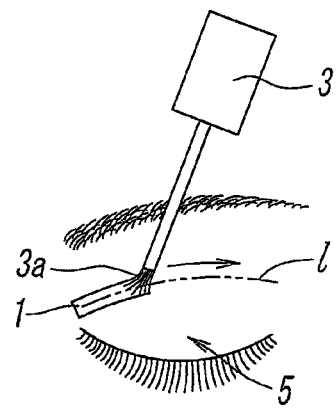
FIG. 3 is a front view showing the eyelid in a state where the solution for forming a double eyelid according to the present invention is being applied thereto.

Then, as illustrated in FIG. 3, the cap 3 is removed from the container 2, and the brush 3a soaked with the solution 1 of the cap 3 successively traces with light touch over the imaginary line I so as to thinly apply the solution 1 onto the skin 5a of the eyelid 5 in a successive-curve form along the edge of the eyelid.

Figure 4:
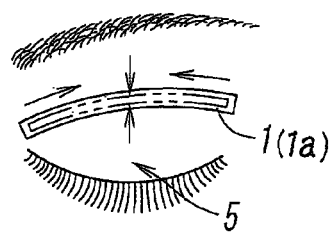
FIG. 4 is a front view showing the eyelid in a state where a film made of base material (fibrous material) is shrinking on the eyelid after applying the solution for forming a double eyelid according to the present invention onto the eyelid.
Figure 5:
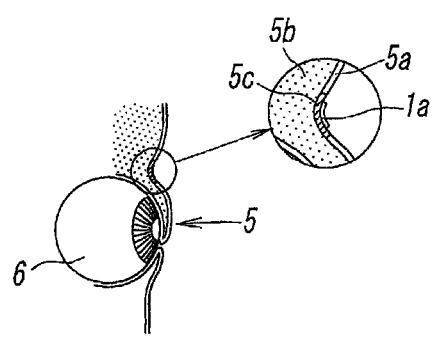
FIG. 5 is a sectional view showing the eyelid in a state where a concavity is formed after applying the solution for forming a double eyelid according to the present invention to the eyelid.

As a result, as illustrated in FIGS. 4 and 5, the solvent of the applied solution 1 is vaporized by the temperature of the eyelid 5. With the vaporization, the fibrous material as the base material forms a thin film 1a on the skin 5a of the eyelid 5 and the entire film 1a shrinks in the state of closely adhering to the skin 5. At this time, as described above, because the shrinking force of the film 1a is larger than the tension (elastic force) on the surface of the skin 5a, the film 1a shrinks against the tension. As described above, because the surface of the skin 5a of the eyelid 5 is formed into a curved state along the surface of the eyeball 6, shrinkage caused by the shrinkage of the film 1a of the skin 5a and the tissue 5b directly thereunder forms successive concaved-groove-like constricted part 5c (hatched portion in FIGS. 5 and 6) at the part on the imaginary line I of the eyelid 5 to which the film 1a is adhered. Further, the film 1a after shrinkage is entirely or almost entirely accommodated in the constricted part 5c, and hence the film 1a is hard to be noticed on appearance even when the eyelid 1 is closed.

Figure 6:
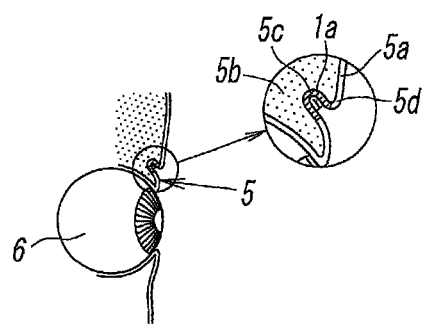
FIG. 6 is a sectional view of the eyelid showing a state of a double eyelid which is formed by applying the solution for forming a double eyelid according to the present invention to the eyelid.
Figure 7:
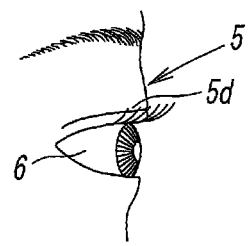
FIG. 7 is a side view of the eyelid showing a state of the double eyelid which is formed by applying the solution for forming a double eyelid according to the present invention to the eyelid.

As a result, as illustrated in FIGS. 6 and 7, when the eyelid 5 is opened, the skin 5a of the eyelid 5 is naturally folded back at the constricted part 5c and a part of the eyelid 5 above the constricted part 5c is folded to overlap with the eyelid to thereby form the fold 5d of the double eyelid along the constricted part 5c. Also at that that time, the film 1a is entirely or almost entirely covered by the fold 5d in the constricted part 5c, and therefore, the usage state thereof is hard to be noticed on the appearance.

Further, the film 1a containing only fibrous material as a base material contributing to formation of the fold 5d of the double eyelid is nonadhesive, does not have ingredients obstructing its resilient shrinkability, and has flexibility. Accordingly, the film 1a is extremely superior in applicability to the movement and expansion and contraction of the skin 5a of the eyelid 5. Therefore, extremely easy formation of a natural and ideal double eyelid also superior in lasting properties is enabled without giving a user displeased feeling and an uncomfortable feeling such as a sticky feeling and a twitch feeling.

It should be noted that, although the solvent of the solution 1 applied on the skin 5a of the eyelid 5 is vaporized by temperature of the eyelid 5, if formation of the double eyelid in shorter time is desired, the vaporization of the solvent may be promoted by utilizing wind of a drier or the like and hot wind.

In addition, although a stick required in order to form the fold of the double eyelid by using conventional cosmetics for forming a double eyelid is basically not necessary in forming a double eyelid by using the above-mentioned solution 1 for forming a double eyelid, this does not restrict use of the stick for more beautifully setting the fold of the double eyelid.

Further, the fibrous material is also superior in affinity for other cosmetics, and hence makeup holds well also on the part onto which the film 1a is adhered. Accordingly, after the formation of the double eyelid, makeup can be applied to the eyelid 5 using a foundation, an eye shadow, and the like when the need arises.

Hereinabove, an embodiment of the solution 1 for forming a double eyelid according to the present invention and a method for forming a double eyelid using the same is described. However, it is needless to say that the present invention is not limited to the above-described embodiment and various design modifications can be made within a range of not departing from the gist of the present invention.

The invention claimed is:

1. An application means and a container for applying a solution for forming a double eyelid to an eyelid, comprising:
    an eyelid applicator, and
    a topical eyelid solution in the container consisting of a solvent and a base material;
    wherein the solvent consists of ethanol and is 75% or more by weight of the solution; and
    the base material dissolvable in the solvent which, when applied to the eyelid, forms a film adhered to the skin of the eyelid with vaporization of the solvent;
    wherein the base material consists of a fibrous material which shrinks with vaporization of the solvent;
    wherein the fibrous material consists of nitrocellulose and the content of the fibrous material in the solution is in the range from 5% to 25% by weight; and
    wherein the film shrinks with shrinkage of the fibrous material to adhere the film to the skin of the eyelid.

2. The application means and the container according to claim 1, wherein a shrinking ratio of the film on the skin of the eyelid is in the range from 10% to 15%.

3. The application means and the container according to claim 1, wherein the film after shrinkage has resilient shrinkability.

4. The application means and the container according to claim 1, wherein the film after shrinkage adheres to the skin of the eyelid but is otherwise non-sticking and non-adhesive.

5. The application means and the container according to claim 1, wherein the solvent vaporizes by contact with body temperature.

6. The application means and the container according to claim 1, wherein the solution consists of nitrocellulose in the amount of 15% by weight of the solution and ethanol in the amount of 85% by weight of the solution.

7. A method for forming a double eyelid, comprising:
    applying a solution to an eyelid to form a film adhered onto the skin of the eyelid, the solution prepared by dissolving in a solvent a fibrous material shrinkable with vaporization of the solvent, the solution consisting of the solvent and the fibrous material;
    vaporizing the solvent to shrink the film made of the fibrous material, and to adhere the film onto the skin of the eyelid
    forming, by shrinkage of the film, a concaved constricted part on the skin of the eyelid; and
    folding back the skin of the eyelid at the constricted part to thereby form a fold of the double eyelid;
    wherein the solvent is 75% or more by weight of the solution and is selected from the group consisting of: ethanol, ethyl acetate, and a mixture of ethanol and ethyl acetate; and
    wherein the fibrous material consists of nitrocellulose.

8. The method of claim 7 wherein the content of the nitrocellulose in the solution is in the range from 5% to 25% by weight.

9. An application means and a container for applying a solution for forming a double eyelid to an eyelid, comprising:
    an eyelid applicator, and
    a topical eyelid solution in the container consisting of a solvent and a fibrous material;
    wherein the solvent is 75% or more by weight of the solution; and
    the fibrous material dissolvable in the solvent which, when applied to the eyelid, shrinks and forms a film adhered to the skin of the eyelid with vaporization of the solvent;
    wherein the solvent is selected from the group consisting of: ethanol, methanol, ethyl acetate, camphor, ether, acetone, or a mixture thereof;
    wherein the fibrous material consists of nitrocellulose and is in the range from 5% to 25% by weight of the solution.

10. The application means and the container according to claim 9, wherein the solvent is selected from the group consisting of: ethanol, ethyl acetate, and a mixture of ethanol and ethyl acetate.

11. The application means and the container according to claim 10, wherein the solvent is ethanol.

\* \* \* \* \*